United States Patent
Phan et al.

(10) Patent No.: US 7,065,737 B2
(45) Date of Patent: Jun. 20, 2006

(54) MULTI-LAYER OVERLAY MEASUREMENT AND CORRECTION TECHNIQUE FOR IC MANUFACTURING

(75) Inventors: Khoi A. Phan, San Jose, CA (US); Bharath Rangarajan, Sunnyvale, CA (US); Bhanwar Singh, Morgan Hill, CA (US)

(73) Assignee: Advanced Micro Devices, Inc, Sunnyvale, CA (US)

( * ) Notice: Subject to any disclaimer, the term of this patent is extended or adjusted under 35 U.S.C. 154(b) by 46 days.

(21) Appl. No.: 10/790,296

(22) Filed: Mar. 1, 2004

(65) Prior Publication Data

US 2005/0193362 A1 Sep. 1, 2005

(51) Int. Cl.
*G06F 17/50* (2006.01)
*G03F 9/00* (2006.01)
*G03C 5/00* (2006.01)

(52) U.S. Cl. .............................. 716/19; 716/4; 716/21; 430/22; 430/30

(58) Field of Classification Search ............ 716/19–21; 382/145; 438/14, 16; 430/5, 22, 30; 356/401
See application file for complete search history.

(56) References Cited

U.S. PATENT DOCUMENTS

| | | | |
|---|---|---|---|
| 6,028,910 A * | 2/2000 | Kirchner et al. | 378/22 |
| 6,197,679 B1 * | 3/2001 | Hattori | 438/636 |
| 6,204,912 B1 * | 3/2001 | Tsuchiya et al. | 355/53 |
| 6,218,200 B1 * | 4/2001 | Chen et al. | 430/5 |
| 6,612,159 B1 * | 9/2003 | Knutrud | 73/105 |
| 6,766,211 B1 * | 7/2004 | Ausschnitt | 700/117 |
| 2002/0041377 A1 * | 4/2002 | Hagiwara et al. | 356/399 |
| 2002/0080364 A1 * | 6/2002 | Monshouwer et al. | 356/508 |
| 2002/0102482 A1 * | 8/2002 | Smith et al. | 430/22 |
| 2002/0137303 A1 * | 9/2002 | Byers et al. | 438/401 |
| 2003/0087192 A1 * | 5/2003 | Gau et al. | 430/311 |
| 2004/0002172 A1 * | 1/2004 | Goo | 438/7 |
| 2004/0109165 A1 * | 6/2004 | Fay et al. | 356/508 |
| 2004/0207097 A1 * | 10/2004 | Carpi et al. | 257/797 |
| 2004/0257571 A1 * | 12/2004 | Mieher et al. | 356/401 |
| 2005/0105092 A1 * | 5/2005 | Ausschnitt et al. | 356/401 |

* cited by examiner

*Primary Examiner*—Paul Dinh
(74) *Attorney, Agent, or Firm*—Amin & Turocy, LLP

(57) ABSTRACT

A system facilitating measurement and correction of overlay between multiple layers of a wafer is disclosed. The system comprises an overlay target that represents overlay between three or more layers of a wafer and a measurement component that determines overlay error existent in the overlay target, thereby determining overlay error between the three or more layers of the wafer. A control component can be provided to correct overlay error between adjacent and non-adjacent layers, wherein the correction is based at least in part on measurements obtained by the measurement component.

30 Claims, 14 Drawing Sheets

FIG. 12
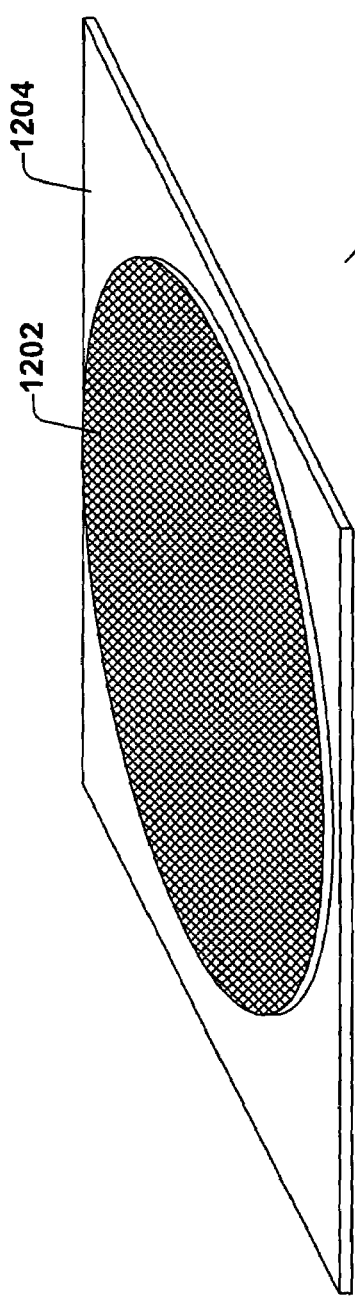
FIG. 14
FIG. 13
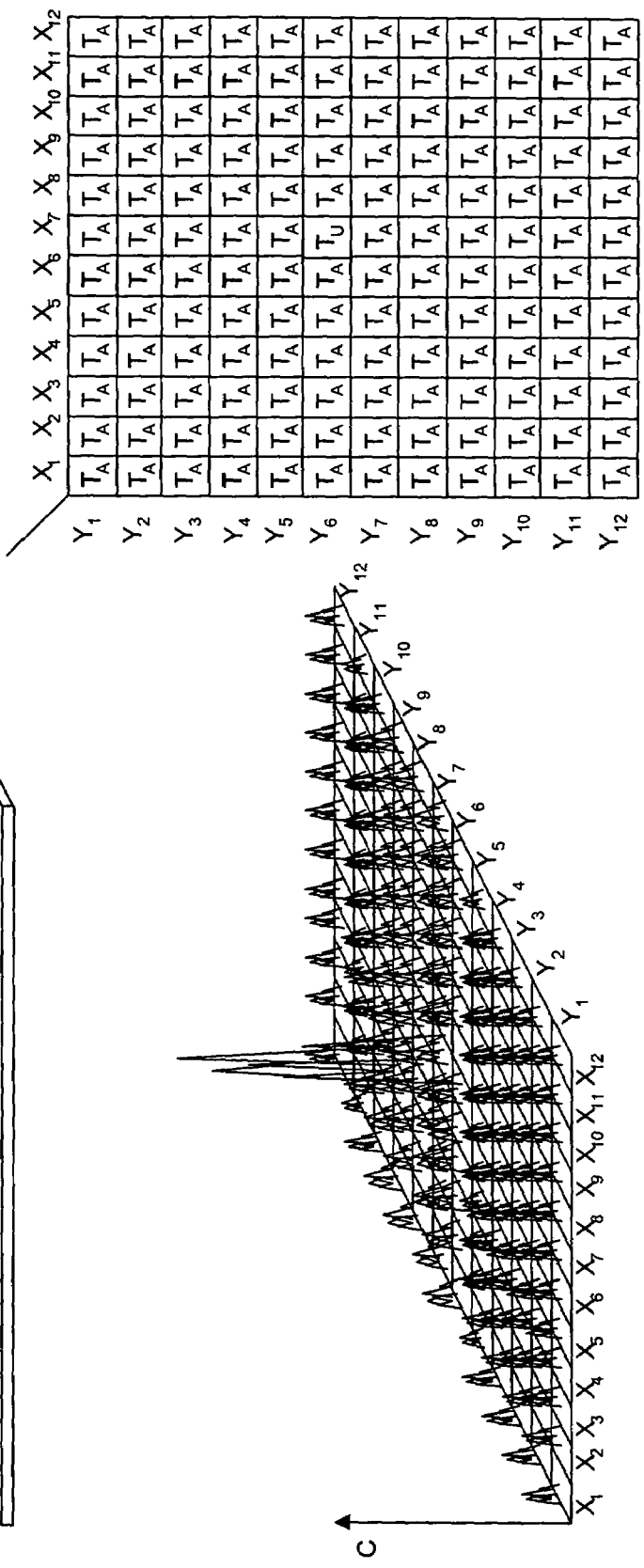

MULTI-LAYER OVERLAY MEASUREMENT AND CORRECTION TECHNIQUE FOR IC MANUFACTURING

TECHNICAL FIELD

The present invention relates generally to monitoring and correcting a semiconductor manufacturing process. More particularly, the invention relates to a system and/or methodology for measuring and correcting overlay of multiple layers on an integrated circuit.

BACKGROUND OF THE INVENTION

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required in integrated circuits (ICs) fabricated on small rectangular portions of the wafer, commonly known as dies. This can include width and spacing of interconnecting lines, spacing and diameter of contact holes, surface geometry such as corners and edges of various features as well as surface geometry of other features. To scale down device dimensions, more precise control of fabrication processes are required. The dimensions of and between features can be referred to as critical dimensions (CDs). Reducing CDs, and reproducing more accurate CDs facilitates achieving higher device densities through scaled down device dimensions and increased packing densities.

Manufacturing semiconductors or ICs typically includes numerous processes (e.g., exposing, baking, developing), during which hundreds of copies of an integrated circuit can be formed on a single wafer, and more particularly on each die of a wafer. In many of these steps, material is overlayed or removed from existing layers at specific locations to form desired circuit structures or elements. Generally, the manufacturing process involves creating several patterned layers on and into a substrate that ultimately forms the complete integrated circuit. This layering process creates electrically active regions in and on the semiconductor wafer surface. Layer to layer alignment and isolation of such electrically active regions can affect precision of structures formed on a wafer. If layers are not aligned within acceptable tolerances, overlay errors can compromise performance of electrically active regions and adversely affecting chip reliability.

Conventional overlay metrology systems and/or methodologies facilitate determining whether two layers lie within the acceptable tolerances. Misalignment can be caused by variations in a lithography process, such as stepper stage variations, lens variations, resist application, develop variations, wafer non-uniformities, etc. Measurements obtained via an overlay metrology tool are utilized to quantify magnitude of error and verify that such magnitude of error decreases as processes are adjusted.

There are two main functions of overlay metrology regarding fabrication of ICs: monitoring performance of lithographic alignment procedure(s) and assisting in setup of a lithography process. For example, overlay metrology can be utilized with a sample wafer to assess overlay performance of a wafer lot. Moreover, overlay measurements can be utilized to optimally configure a stepper system prior to operation, and can later be employed to maintain optimal stepper performance via periodic overlay evaluation.

Overlay error has typically been measured and analyzed only between adjacent layers. Turning now to the drawings, FIG. 1 illustrates a prior art method 100 of measuring overlay error. As a first layer is added to a wafer, a square layer 102 utilized as a portion of an overlay target 104 is created outside of IC design areas at various positions on the wafer. As a second layer is added to the wafer, a smaller second square layer 106 utilized as a portion of the overlay target 104 corresponding to the second layer of the IC is placed atop the first portion 102 of the overlay target 104, and a larger layer 108 utilized as a portion of a second overlay target 110 likewise corresponding to the second layer of the wafer is created (e.g., dashed lines indicate layers of overlay targets representing a same layer of the wafer). As a third layer of the wafer is created atop the second layer of the wafer, a smaller layer 112 utilized as a portion of the second overlay target 110 is placed on the larger second layer 108 of the overlay target 110. A larger third layer 114 utilized as a portion of an overlay target 116 is also created. The process continues until a pre-determined amount of layers have been created. Thus the layers 102, 106, 108, 112, and 114 enable measurement of overlay error (e.g., distance between center points of the overlay targets and rotational difference between such targets) between the first and second layers and the second and third layers, respectively. If overlay error between adjacent layers is below a pre-defined threshold tolerance, the process(es) creating the layers are deemed satisfactory.

However, in ICs with multiple layers, repeated overlay error(s) (even slight error(s)) between multiple layers can result in compromised performance of a completed IC. Turning briefly to FIG. 2, an acceptable overlay error 200 that can occur between two overlay targets is illustrated. Overlay target 202 corresponds to a first layer of an IC, and overlay target 204 corresponds to a second layer of an IC, wherein the overlay target 202 has a desirable width of $d_1$ and the overlay target 204 has a desirable width of $d_2$. As illustrated by dashed lines 206 and 208, variations in a process are accounted for via permitting the overlay target 202 to have a width as small as $d_3$ and the overlay target 204 to have a width as large as $d_4$. In conventional overlay metrology methods, intersection of the dashed lines 206 and 208 indicate an unacceptable overlay between two layers corresponding to the overlay targets 202 and 204. A distance $d_5$ indicates an amount of overlay error between layers represented by overlay targets 202 and 204 (e.g., distance between center points of the overlay targets 202 and 204). Moreover, a rotation of α between such overlay targets 202 and 204 is also acceptable provided that the rotation α is below a pre-defined threshold. If the overlay targets 202 and 204 indicate an unacceptable amount of overlay error and/or rotation between two layers corresponding to the overlay targets 202 and 204, corrective measures can be taken regarding such two layers.

Turning now to FIG. 3, a plurality of IC devices and/or layers of a wafer 300 are illustrated, wherein the overlay error exemplified in FIG. 2 is repeated throughout such plurality of IC devices and/or layers 300. For example, the overlay error 200 (FIG. 2) exists between IC device 302 and IC device 304, wherein the IC devices 302 and 304 are located within adjacent layers. A substantially similar overlay error exists between IC devices 304 and 306, 306 and 308, 308 and 310, and 310 and 312. If fabrication device(s) and/or process(es) causing such overlay error 200 are not modified to mitigate such overlay errors, a large aggregated discrepancy results between non-adjacent devices in non-adjacent layers. For example, the device 312 is significantly rotated and displaced through a plurality of layers from device 302, while such devices 302 and 312 would ideally be approximately concentric. Such substantial rotation and displacement between layers and/or devices can compromise IC performance. Thus, a more robust overlay metrology system and/or methodology to analyze multiple layers of an IC and correct overlay error between such layers is desirable to mitigate the aforementioned deficiencies of conventional systems and/or methods.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention facilitates measurement and correction of overlay error between multiple layers of an integrated circuit on a wafer, thus mitigating repetitive occurrences of overlay error over a plurality of layers. Furthermore, the present invention allows for design specifications relating to overlay between multiple layers within a wafer. Overlay target(s) that represent overlay between multiple layers are provided to enable measurement of overlay between such layers. The overlay targets can be of a box-in-box structure, frame-in frame structure, segmented frame structure, grating structure overlay targets or other suitable periodic structure overlay marks, or any other suitable structure that enables representation of overlay between more than two layers of a wafer. The overlay target(s) can be analyzed to determine an existing amount of overlay error between adjacent and non-adjacent layers on a wafer. For example, optical microscopy, scatterometry, scanning electron microscopy, and Fourier transform infrared scatterometry can be employed in connection with measuring overlay error between multiple layers. Furthermore, when utilizing periodic structure overlay marks, overlay error can be calculated via determining pitch of such overlay marks, which can be user-defined or measured in real time.

Measurements relating to overlay error between multiple layers can be utilized to correct such overlay error. For instance, a control system can be provided, wherein such control system can utilize the overlay error measurements as feedback and/or feed-forward data, thus facilitating correction of overlay error between multiple layers of a wafer via controlling fabrication component(s) utilized in connection with a fabrication process. For example, temperature within a process chamber can be manipulated to facilitate correction of overlay error to design specifications between multiple layers.

In accordance with another aspect of the present invention, an importance of overlay in a particular dimension can be determined and more correction can be provided in such dimension. For instance, overlay between multiple layers can be more pertinent in a specific dimension given a particular integrated circuit (IC) design, and the present invention can provide corrective resources accordingly. More particularly, if overlay between multiple layers is more important in a first dimension when compared to second dimension, more correction will be provided in the first dimension and less will be provided in the second dimension. In accordance with another aspect of the present invention, a model for correcting overlay in multiple layers of a wafer can be utilized in connection with the present invention. For instance, a large correction in a first dimension between non-adjacent layers correlates to a large correction in a dimension perpendicular to the first dimension in adjacent layers. Likewise, a small correction in the first dimension between non-adjacent layers correlates to a small correction in the second dimension between adjacent layers of an IC.

To the accomplishment of the foregoing and related ends, the invention then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

FIG. 12 illustrates a perspective view of a grid mapped wafer according to one or more aspects of the present invention.

FIG. 13 illustrates plots of measurements taken at grid mapped locations on a wafer in accordance with one or more aspects of the present invention.

FIG. 14 illustrates a table containing entries corresponding to measurements taken at respective grid mapped locations on a wafer in accordance with one or more aspects of the present invention.

DETAILED DESCRIPTION OF THE INVENTION

Figure 1:
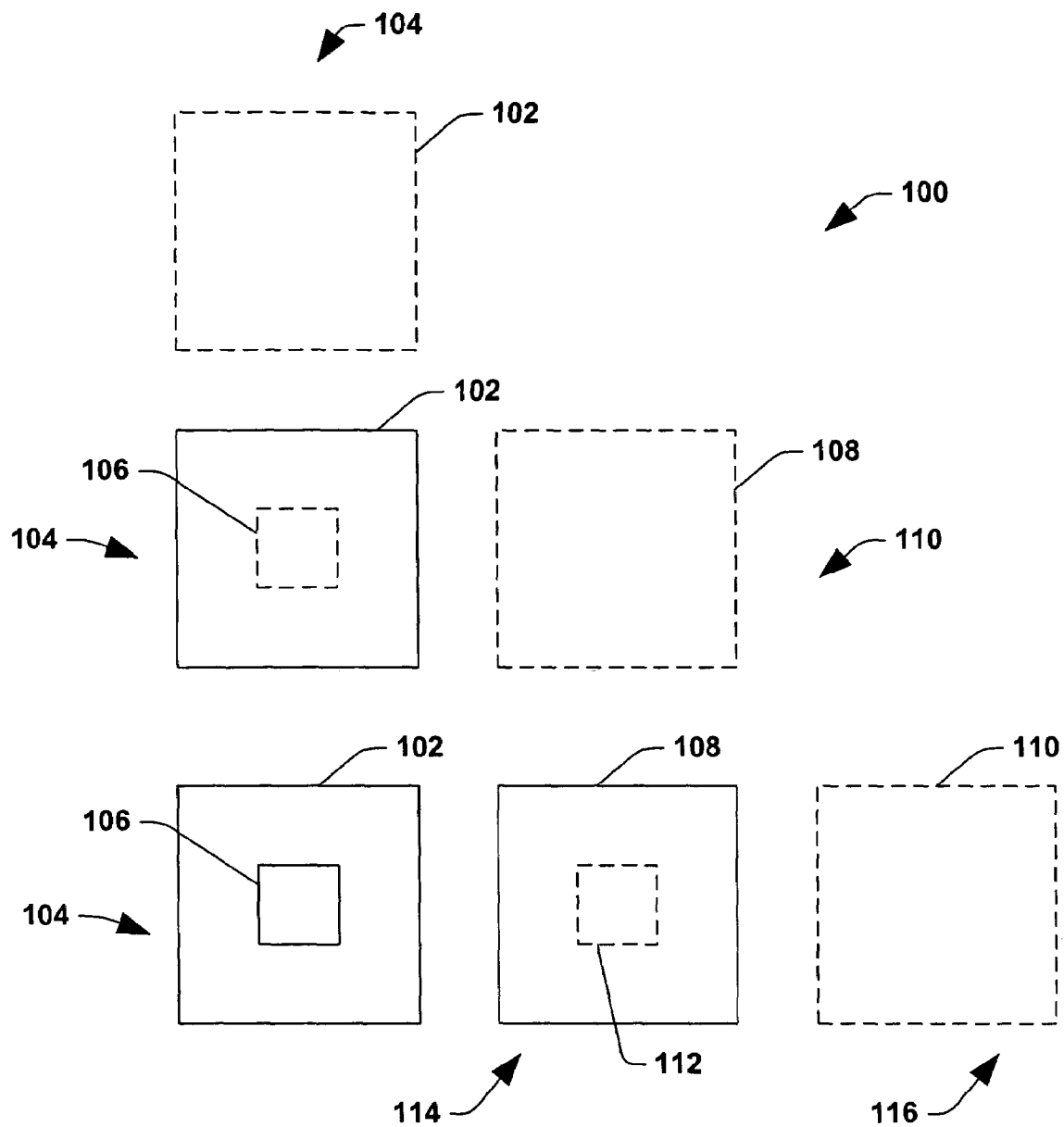
FIG. 1 is a diagram of overlay targets utilized in prior art overlay metrology systems.
Figure 2:
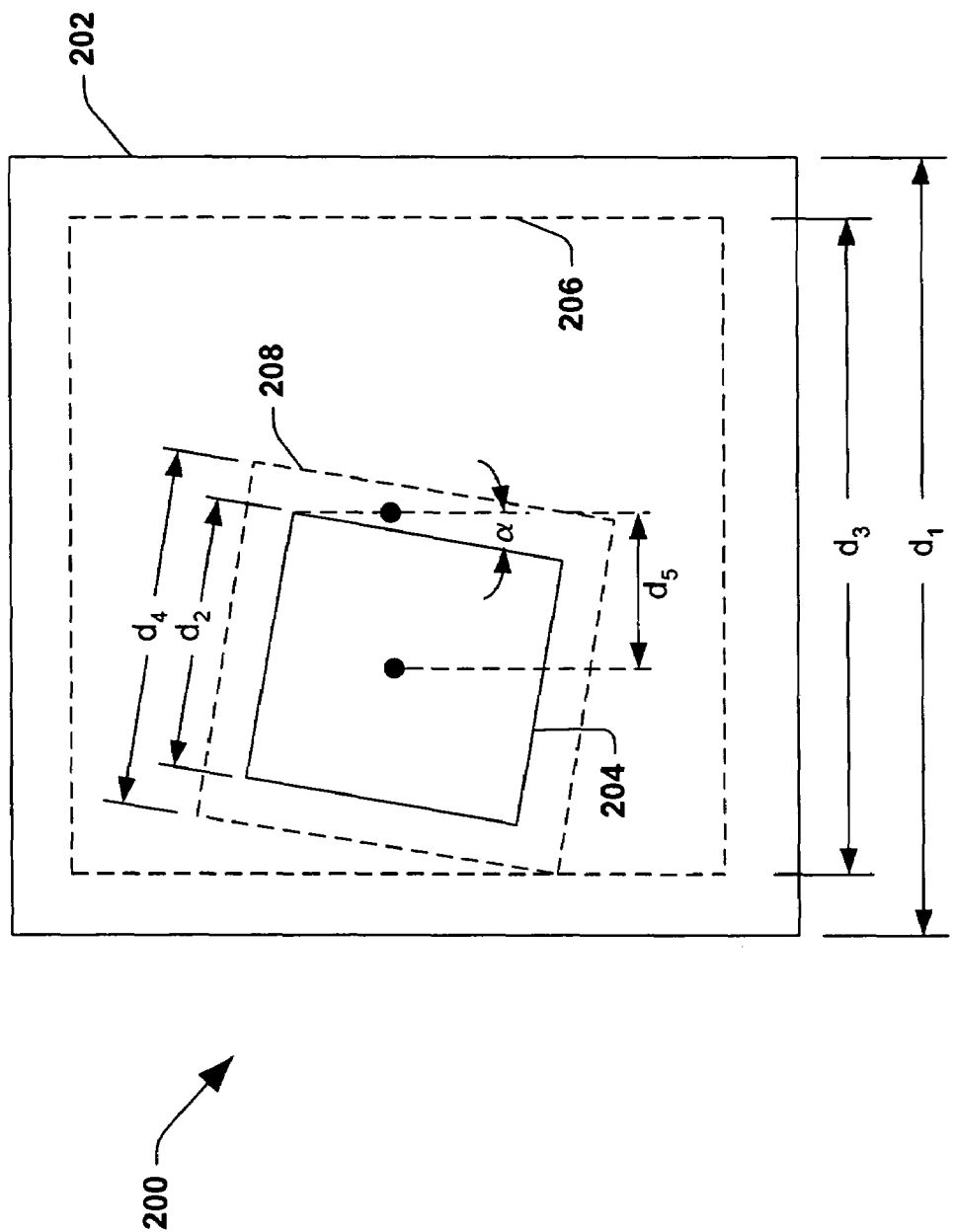
FIG. 2 is an exemplary diagram of overlay error that can occur between adjacent layers.
Figure 3:
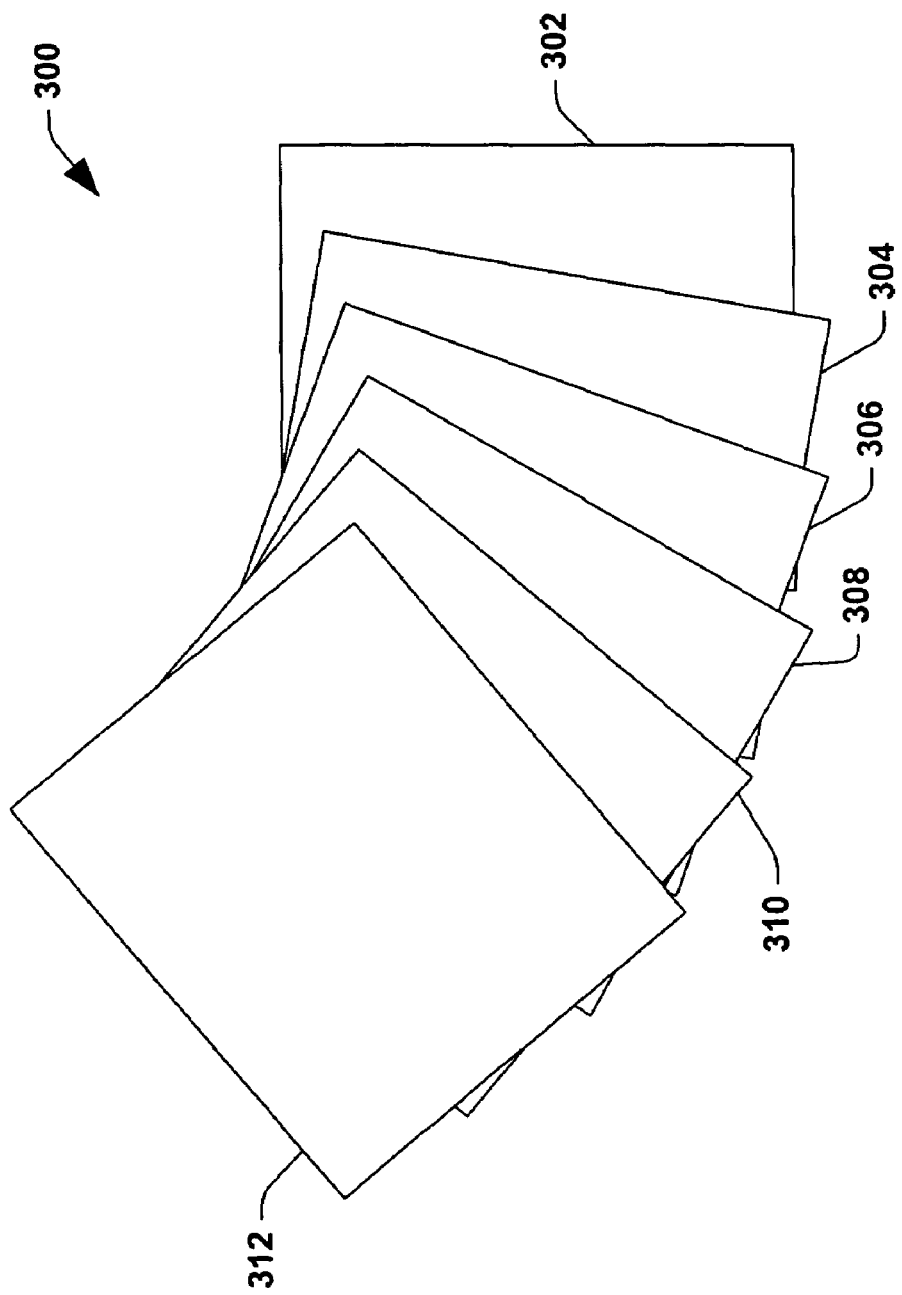
FIG. 3 is an exemplary diagram of overlay error that can occur between multiple layers utilizing overlay error measurement and correction systems and/or methodologies of the prior art.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "computer component" is intended to refer to a computer-related entity, either hardware, a combination of hardware and software, software, or software in execution. For example, a computer component may be, but is not limited to being, a process running on a processor, a processor, an object, an executable, a thread of execution, a program, and/or a computer. By way of illustration, both an application running on a server and the server can be a computer component. One or more computer components may reside within a process and/or thread of execution and a component may be localized on one computer and/or distributed between two or more computers.

It is to be appreciated that various aspects of the present invention can employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) can be employed. It is to be further understood that the term "overlay target" can refer to a target representing a single layer of a wafer as well as a target representing multiple layers of a wafer.

Figure 4:
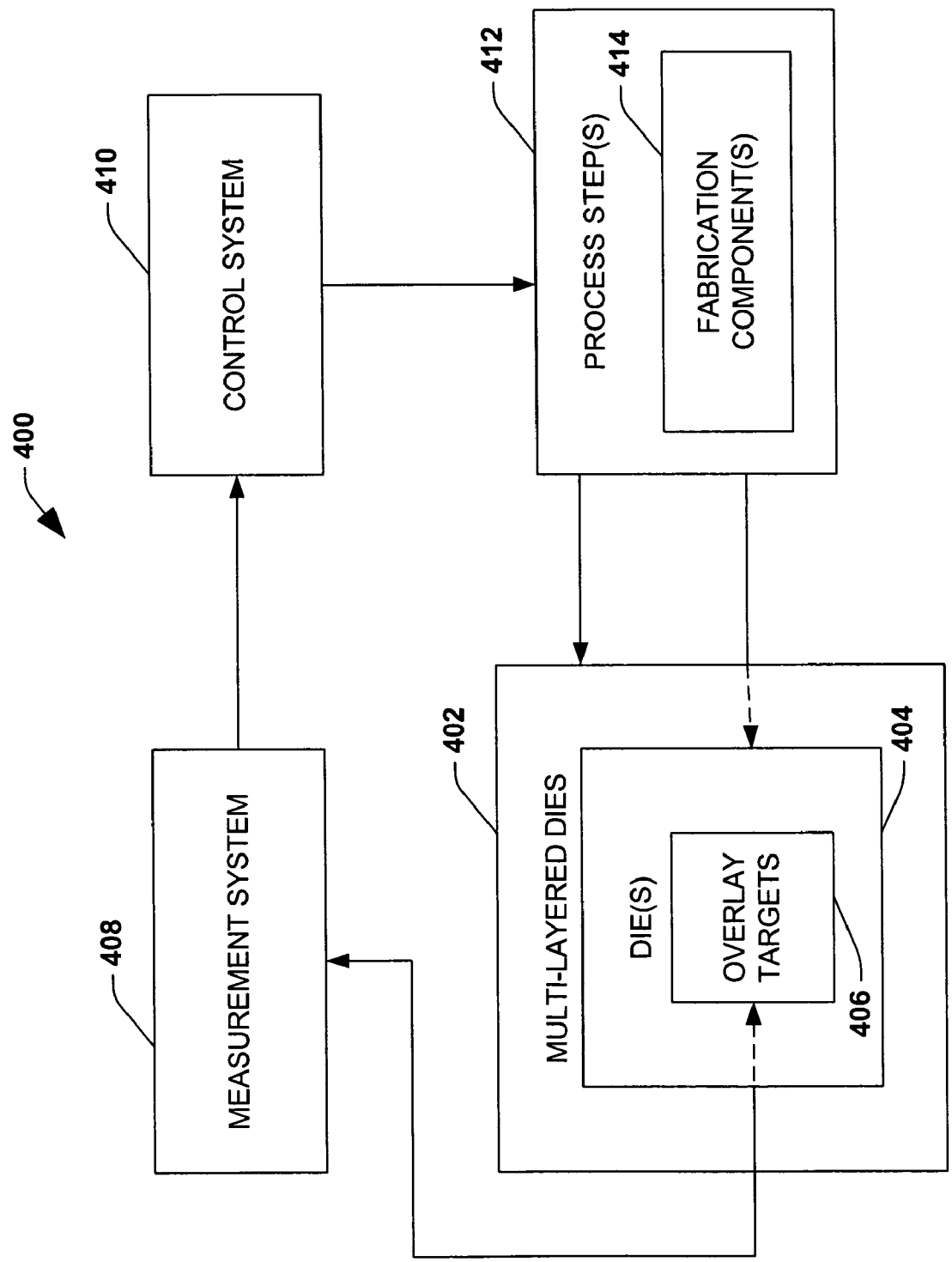
FIG. 4 is a block diagram of an overlay metrology and correction system in accordance with an aspect of the present invention.

Turning now to FIG. 4, an exemplary system 400 for measuring and correcting overlay in multi-layered wafer(s) (dies) is illustrated. The system 400 includes one or more multi-layered wafer(s) 402, wherein the wafer(s) comprise a plurality of dies 404 that are therefore also multi-layered. One or more of the die(s) 404 can be associated with overlay target(s) 406 which correspond to multiple (e.g., more than two) layers of the die(s) 404. For example, the overlay target 406 can be a box-in-box structure, wherein each box corresponds to a layer of the die 404, and the overlay target 406 includes more than two boxes. Other similar overlay target structures, such as frame-in-frame and segmented frame structures, are also contemplated by the present invention.

A measurement system 408 is employed to measure and/or analyze the overlay target(s) 406. For example, the measurement system 408 can measure and/or analyze overlay targets representing adjacent layers of the die(s), as well as non-adjacent layers of the die(s). In a more specific example, the overlay target(s) 406 can comprise four boxes, each box associated with a disparate layer of the die(s) 404. The measuring system 408 can measure and/or analyze overlay of adjacent layers as well as overlay between a first and third layer, first and fourth layer, and second and fourth layer. While the previous example utilizes four as a number of layers, it is to be appreciated that the measurement system 408 can be employed to measure and/or analyze overlay targets representing any number of layers over two. The measuring system 408 can utilize any suitable measurement and/or analysis methodologies to obtain information from the overlay target(s) 406. For example, optical microscopy can be employed in connection with the present invention to facilitate measurement and/or analysis of the overlay target(s) 406. Alternatively, scanning electron microscopy, scatterometry, Fourier transform infrared scatterometry (FTIR), as well as any other suitable microscopic measuring and/or analysis techniques are contemplated by the present invention. The measurements can, in particular, be utilized for generating feedback and/or feed-forward data for mitigating overlay and/or bringing critical dimensions within acceptable tolerances. FTIR is a technique that uses an interferometer for data collection and a digital Fourier transformation to process the data. In the context of semiconductor fabrication, IR radiation is passed through a wafer sample. Some of the infrared radiation is absorbed by the sample material and some of it is passed through (or transmitted). The resulting spectrum represents the molecular absorption and transmission, creating a molecular fingerprint of the wafer sample. Like a fingerprint, no two unique molecular structures produce the same infrared spectrum. This makes infrared spectroscopy useful for several types of analysis.

Measurements obtained by the measurement system 408 can then be received by a control system 410 that facilitates correction of overlay error between three or more layers represented by the overlay target(s) 406. For example, overlay between three or more layers can be corrected according to design rule requirements as well as for optimal fabrication device performance. Moreover, the control system 410 can utilize measurements obtained via the measurement system 408 to determine appropriate corrective measures along dimension(s) defining the layers. For instance, the control system 410 can utilize measurements and design rule requirements relating to the wafer 402 to determine a dimension in which correction is most important. More particularly, if correct overlay in a x-dimension is more important than correct overlay in a y-dimension between two layers (adjacent or non-adjacent), the control system 410 will facilitate application of a greater amount of correction in the x-dimension than the y-dimension. Furthermore, the control system 410 can utilize measurements obtained by the measurement system 412 to generate control commands that are employed to correct rotational overlay error.

The control system 410 can thereafter relay control commands that effectuate desirable correction to particular process step(s) 412, such as an etching step, lithography step, etc. Moreover, as process step(s) 412 utilize fabrication component(s) 414, the control system 410 can directly control particular fabrication component(s) 414 in connection with correcting overlay error. It is to be appreciated that any of a variety of fabrication components and/or operating parameters associated therewith can be selectively controlled based at least in part upon the readings taken by the measuring system 408. By way of example and not limitation, this can include, but is not limited to, temperatures associated with the process step(s) 412, pressures associated with the process step(s) 412, concentration of gases and chemicals within the process step(s) 412, composition of gases, chemicals and/or other ingredients within the process step(s) 412, flow rates of gases, chemicals and/or other ingredients within the process 412 step(s), timing parameters associated with the process step(s) 412 and excitation voltages associated with the process step(s) 412. By way of further example, parameters associated with high-resolution photolithographic components utilized to develop ICs with small closely spaced apart features can be controlled to correct overlay error. In general, lithography refers to processes for pattern transfer between various media and in semiconductor fabrication, a silicon slice, the wafer, is coated uniformly with a radiation-sensitive film, the photoresist. The photoresist-coated substrate is baked to evaporate any solvent in the photoresist composition and to fix the photoresist coating onto the substrate. An exposing source (e.g., light, x-rays, or an electron beam) illuminates selected areas of the surface of the film through an intervening master template for a particular pattern. The photoresist coating is generally a radiation-sensitized coating suitable for receiving a projected image of the subject pattern. Once the image from the intervening master template is projected onto the photoresist, it is indelibly formed therein.

Light projected onto the photoresist layer during photolithography changes properties (e.g., solubility) of the layer such that different portions thereof (e.g., the illuminated or un-illuminated portions, depending upon the photoresist type) can be manipulated in subsequent processing steps. For example, regions of a negative photoresist become insoluble when illuminated by an exposure source such that the application of a solvent to the photoresist during a subsequent development stage removes only non-illuminated regions of the photoresist. The pattern formed in the negative photoresist layer is, thus, the negative of the pattern defined by opaque regions of the template. In contrast, regarding a positive photoresist, illuminated regions of the photoresist become soluble and are removed via application of a solvent during development. Thus, the pattern formed in the positive photoresist is a positive image of opaque regions on the template. Controlling the degree to which a photoresist is exposed to illumination (e.g., time, intensity) can at least partially correct overlay error.

A type of illumination utilized to transfer the image onto a wafer can also be controlled to correct overlay error between adjacent and non-adjacent layers. For instance, as feature sizes are driven smaller and smaller, limits are approached due to wavelengths of optical radiation. As such, type and wavelength of radiation utilized for pattern transfers can be controlled to correct overlay error. For instance, radiation having more conducive wavelengths (e.g., extreme ultraviolet (EUV) and deep ultraviolet (DUV) radiation having wavelengths within the range of 5–200 nm) can be utilized for lithographic imaging in an effort to accurately achieve smaller feature sizes. However, such radiation can be highly absorbed by the photoresist material. Consequently, the penetration depth of the radiation into the photoresist can be limited. The limited penetration depth requires use of ultra-thin photoresists so that the radiation can penetrate the entire depth of the photoresist in order to effect patterning thereof. The performance of circuits formed through photolithographic processing is, thus, also affected by the thickness of photoresist layers. The thickness of photoresist layers can be reduced through chemical mechanical polishing (CMP). In general, CMP employs planarization techniques wherein a surface is processed by a polishing pad in the presence of an abrasive or non-abrasive liquid slurry. The slurry employed reacts with the photoresist at the surface/subsurface range. Preferably the degree of reaction is not great enough to cause rapid or measurable dissolution (e.g., chemical etching) of the photoresist, but merely sufficient to cause a minor modification of chemical bonding in the photoresist adequate to facilitate surface layer removal by applied mechanical stress (e.g., via use of a CMP polishing pad). Thus, overlay error can be corrected by controlling concentration, rate of flow and degree of abrasiveness of slurry applied during the CMP process as well as amount of pressure applied between a polishing pad and wafer during such process.

Depending upon the resist system utilized, post exposure baking may also be employed to activate chemical reactions in the photoresist to affect image transfer. The temperatures and/or times that portions of the wafer are exposed to particular temperatures can be controlled to regulate the uniformity of photoresist hardening (e.g., by reducing standing wave effects and/or to thermally catalyze chemical reactions that amplify the image). Higher temperatures can cause faster baking and faster hardening, while lower temperatures can cause slower baking and correspondingly slower hardening. The rate and uniformity of photoresist hardening can affect overlay error, such as, for example, by altering the consistency of a line width. Accordingly, time and temperature parameters can be controlled during post exposure baking to affect overlay error.

Operating parameters of an etching stage can similarly be controlled to achieve desired critical dimensions and to mitigate overlay error between more than two layers. After illumination, the pattern image is transferred into the wafer from the photoresist coating in an etching stage wherein an etchant, as well as other ingredients, are applied to the surface of the wafer by an excitation voltage or otherwise. The etchant removes or etches away portions of the wafer exposing during the development process. Portions of the wafer under less soluble areas of the photoresist are protected from the etchants. The less soluble portions of the photoresist are those portions that are not affected by the developer during the development process and that are not affected by the etchant during the etching process. These insoluble portions of the photoresist are removed in subsequent processing stage(s) to completely reveal the wafer and the pattern(s) formed therein. The concentration of materials utilized in etching can thus be controlled to achieve desired critical dimensions and to mitigate overlay for instance by affecting the accuracy with which selected portions of the wafer are etched away.

Parameters relating to the type of template utilized to transfer an image onto a wafer can also be controlled to correct overlay error. Where the template is a reticle, the pattern is transferred to only one (or a few) die per exposure, as opposed to where the template is a mask and all (or most) die on the wafer are exposed at once. Multiple exposures through a reticle are often performed in a step and scan fashion. After each exposure, a stage to which the wafer is mounted is moved or stepped to align the next die for exposure through the reticle and the process is repeated. This process may need to be performed as many times as there are die in the wafer. Thus, stepper movement can be controlled to correct overlay error (e.g., by feeding fed forward and/or backward measurements to a stepper motor). The pattern formed within the reticle is often an enlargement of the pattern to be transferred onto the wafer. This allows more detailed features to be designed within the reticle. Energy from light passed through the reticle can, however, heat the reticle when the image is exposed onto the wafer. This can cause mechanical distortions in the reticle due to thermal expansion and/or contraction of the reticle. Such distortions may alter the geometry of intricate features (e.g., by narrowing a line) and/or interfere with layer-to-layer registration to such a degree that a resulting circuit does not operate as planned when the image is transferred onto the wafer. Moreover, since the pattern is usually an enlargement of the pattern to be transferred onto the wafer, it typically has to be reduced (e.g., via a de-magnifying lens system) during the lithographic process. Shrinking an already distorted feature (e.g., a narrowed line) can have a deleterious effect on critical dimensions and overlay. Thus, while such a template may be effective to transfer more intricate pattern designs, it calls for highly accurate alignment and imaging to correct overlay errors and maintain critical dimensions to within acceptable tolerances. Temperature controls can thus be employed to mitigate thermally induced mechanical distortions in the reticle.

Additionally, parameters relating to film growth or deposition components (e.g., producing metals, oxides, nitrides, poly, oxynitrides or insulators) can be controlled to correct overlay error. Such films can be formed through thermal oxidation and nitridation of single crystal silicon and polysilicon, the formation of silicides by direct reaction of a deposited metal and the substrate, chemical vapor deposition (CVD), physical vapor deposition (PVD), low pressure CVD (LPCVD), plasma enhanced CVD (PECVD), rapid thermal CVD (RTCVD), metal organic chemical vapor deposition (MOCVD) and pulsed laser deposition (PLD). The rates of flow, temperature, pressures, concentrations and species of materials supplied during the semiconductor fabrication process can thus be controlled to govern film formation that bears on overlay.

Moreover, it is to be understood that the present invention facilitates simultaneous correction of overlay between multiple targets regarding various process variables. For example, tool-induced shift can be corrected simultaneously with tool-to-tool overlay via the control component 410 controlling the process steps 412. Furthermore, the measurements obtained by the measurement system 408 can be simultaneously utilized as both feed-back and feed-forward information, thus enabling correction of overlay of multiple wafers simultaneously.

Figure 5:
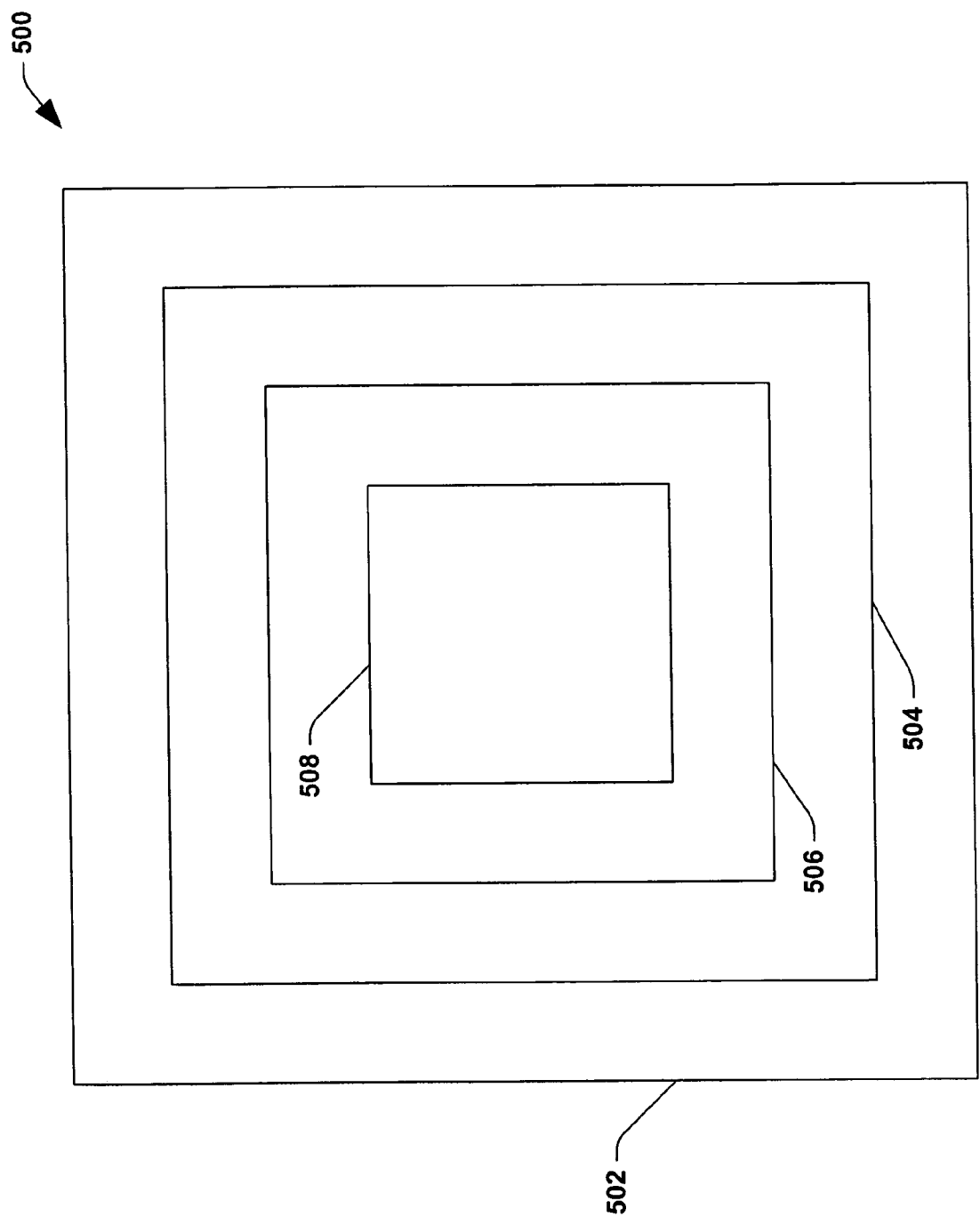
FIG. 5 is an exemplary overlay target that can be utilized in accordance with one aspect of the present invention.

Turning now to FIG. 5, an exemplary box-in-box overlay target 500 is illustrated. The overlay target 500 includes boxes 502–508 that are each associated with a layer in an IC. More specifically, box 502 is associated with a first layer of an IC, box 504 is associated with a second layer of the IC, box 506 is associated with a third layer of the IC, and box 508 is associated with a fourth layer of the IC. The boxes 502–508 are created concurrently with a layer that they represent (e.g., box 502 is created when a first layer is created). Creation of the overlay target 500 enables measurement and correction of overlay error between adjacent and non-adjacent layers of the IC. Overlay error is defined as a planar distance from a center of one box to a center of another box, and is determined via utilizing symmetry of each box, such that error associated with edge determination will tend to cancel from each side of the box. Thus, to compute overlay error between box 502 and box 506, the center of the box 502 is first determined, followed by the center of the box 506. A distance and angle between such centers is the overlay error between the boxes 502 and 506, and is thus the overlay error between the layers represented by such boxes 502 and 506.

In a more particular example, overlay error in a x-direction and y-direction, as well as rotational overlay error, can be measured between box 508 and box 506. Thereafter overlay error between boxes 508 and 504 can be determined in a substantially similar manner. It can be discerned that overlay error can thus be determined between any two boxes in the overlay target 500, wherein the boxes 502–508 each represent a layer in an IC (e.g., overlay error between boxes represents overlay error between layers). After overlay error has been determined, if more importance resides with correcting a third layer (represented by box 506) with respect to a first layer (502) in an x-direction, more correction will be applied in the x-direction and less will be applied in a y-direction. Moreover, a large correction in the x-direction for non-adjacent layers typically will result in a large correction in the y-dimension for adjacent layers. For example, if a large overlay correction is desirable between layers 502 and 508 along a x-direction, a large overlay correction will be desirable between layers 506 and 508 in a y-direction. Likewise, a small correction in the x-direction for non-adjacent layers typically will result in a small correction in the y-dimension for adjacent layers.

Figure 6:
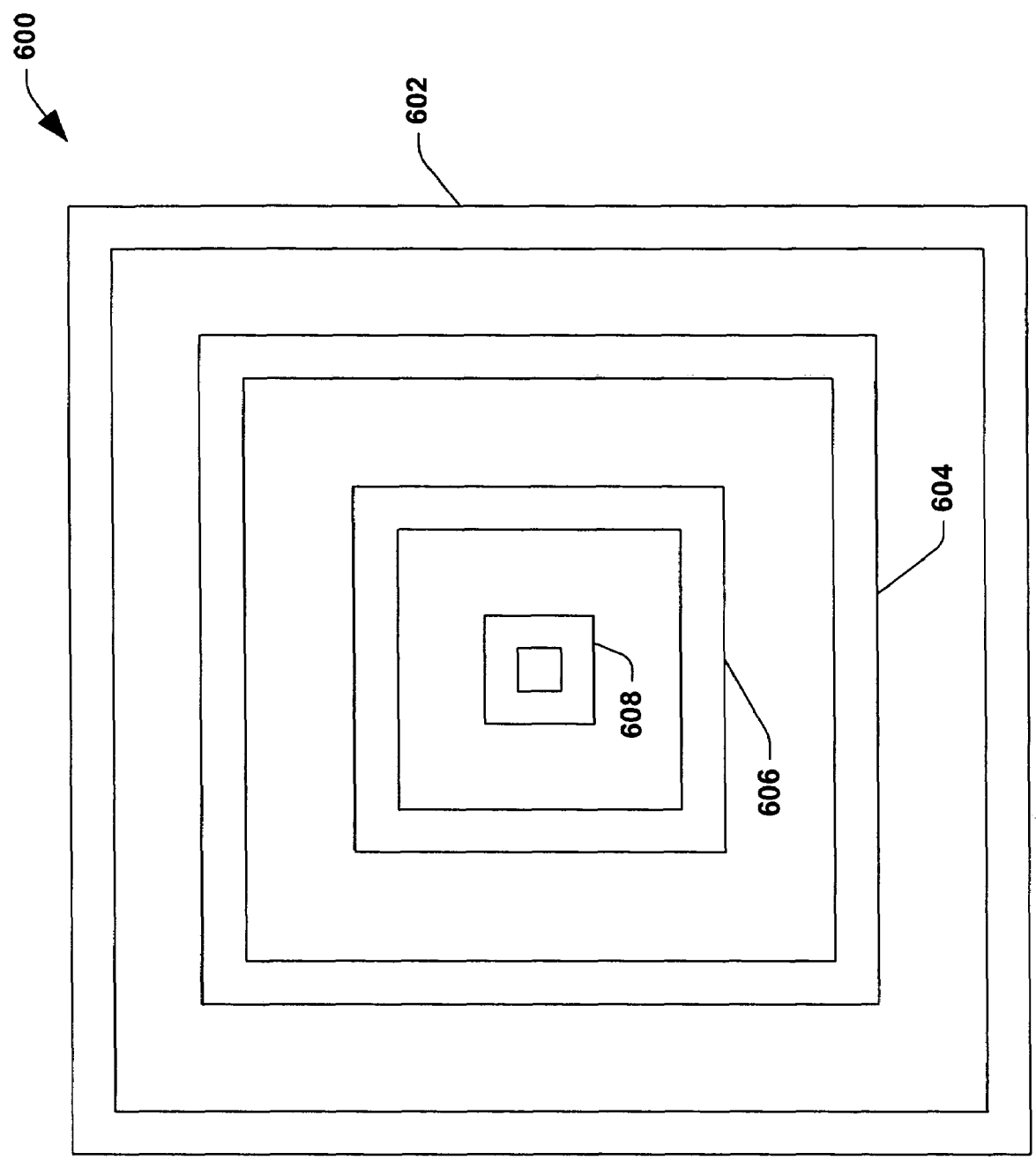
FIG. 6 is an exemplary overlay target that can be utilized in accordance with one aspect of the present invention.
Figure 7:
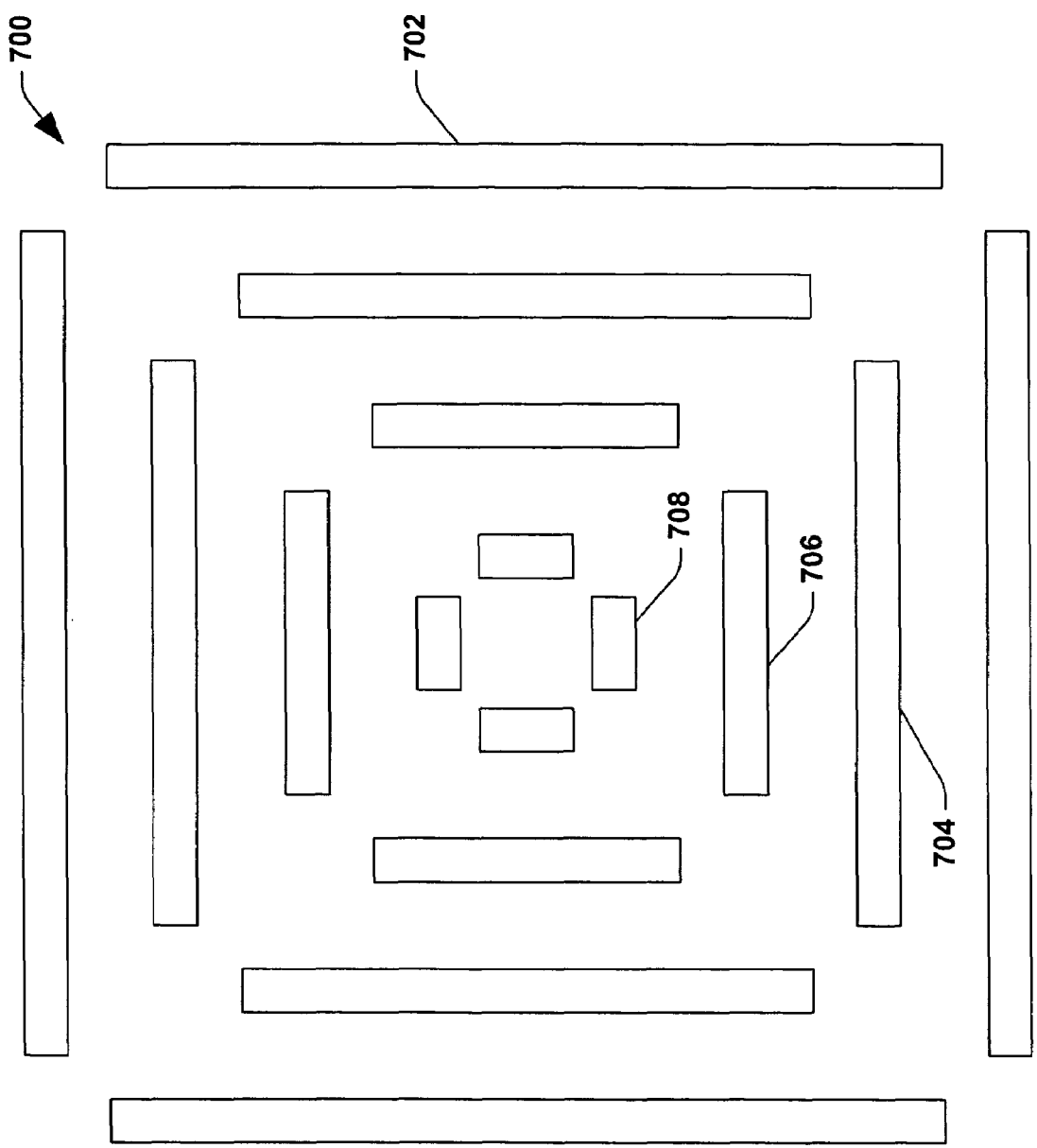
FIG. 7 is an exemplary overlay target that can be utilized in accordance with one aspect of the present invention.

Now referring to FIGS. 6 and 7, exemplary overlay targets 600 and 700 are illustrated. The overlay target 600 is a frame-in-frame target, wherein each frame represents a disparate layer of an IC. For example, frame 602 represents a first layer, frame 604 represents a second layer, frame 606 represents a third layer, and frame 608 represents a fourth layer. It is to be understood, however, that more than four layers can be represented by a overlay target in connection with the present invention. The overlay target 700 (FIG. 7) is a segmented frame target. Symmetrical segments represent disparate layers of an IC (e.g., segment 702 represents a first layer, segment 704 represents a second layer, segment 706 represents a third layer, and segment 708 represents a fourth layer). A segmented frame overlay target structure can be beneficial due to a lack of corners, which make the segmented frame structure less susceptible to resist flow or viscosity-related buildup. The segments and frames of the overlay targets 600 and 700 are created at substantially the same time as a layer a segment represents. For instance, segment 704 is created at a substantially similar time as a second layer of an IC is created. Thus the frames 602–608 and segments 702–708 accurately depict overlay error that occurs between layers of an IC. Overlay error is determined for frame-in-frame and segmented frame overlay targets in a manner substantially similar of that utilized to determine overlay error in a box-in-box structure (e.g., symmetry of the frames and segments is utilized to determine a center point).

In accordance with one aspect of the present invention, the overlay targets 600 and 700 can be measured and/or analyzed to determine overlay error between adjacent and non-adjacent layers. A control system (not shown) can be provided to determine appropriate overlay correction in a x-dimension and y-dimension, wherein fabrication rules and overlay error allowance can be accounted for by the control system (e.g., if proper overlay is more important between particular layers in a particular direction, apply more correction in the particular direction for the particular layers). Similar to the box-in-box overlay structure, a large overlay correction between non-adjacent layers in the x-direction will correlate to a large overlay correction between adjacent layers in the y-direction. Likewise, a small overlay correction between adjacent layers in the y-direction will correlate to a small overlay correction in the x-direction.

Figure 8:
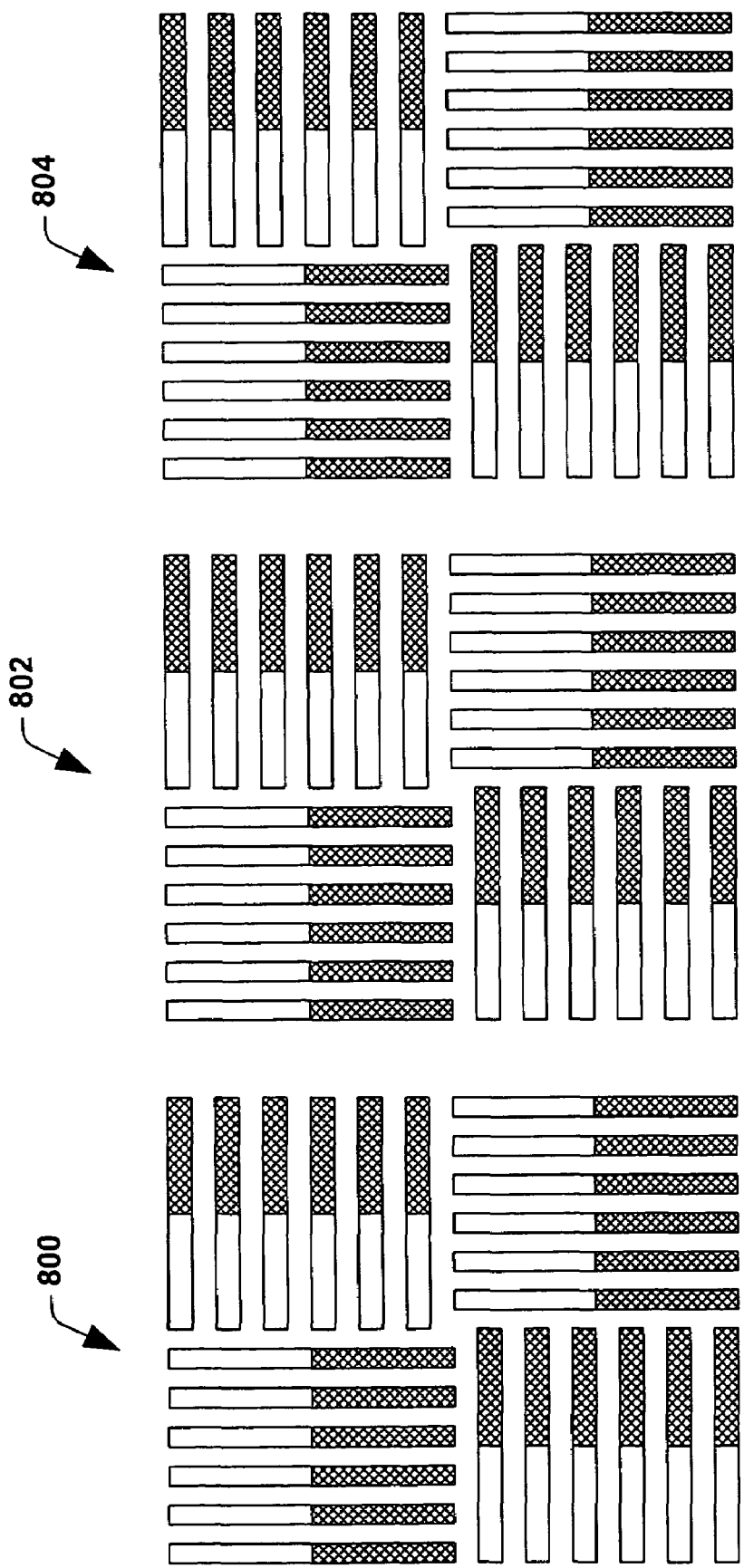
FIG. 8 is an exemplary overlay target that can be utilized in accordance with one aspect of the present invention.

Now regarding FIG. 8, exemplary periodic structure overlay marks 800, 802, and 804 (e.g., periodic grating marks) are illustrated, wherein the overlay marks 800, 802, and 804 represent disparate layers of a wafer. While displayed adjacently, it is to be understood that the periodic structure overlay marks 800, 802 and 804 are typically generated concentrically (e.g., similar to the box-in-box and frame-in-frame structures), and overlay error is determined by measuring displacement between centers of symmetry of such overlay marks 800, 802, and 804. The overlay marks 800, 802 and 804 can facilitate more precise overlay error measurement and correction between multiple layers when compared to conventional box-in-box and frame-in-frame structures. For instance, overlay error is typically measured when box-in-box structures are utilized via computing number of pixels between centers of adjacent boxes within a digital image. In contrast, pitch of the overlay marks 800, 802, and 804 is a unit of measure for determining overlay error, which can be user-defined and/or measured in real time.

In accordance with one aspect of the present invention, the overlay marks 800, 802, and 804 can include coarse segmentation, fine segmentation, and/or a combination of coarse and fine segmentation. The present invention enables measurement of overlay error between both adjacent and non-adjacent periodic structure overlay marks 800, 802, and 804. For instance, overlay mark 800 can represent a first layer, overlay mark 802 can represent a second layer, and overlay mark 804 can represent a third layer. Overlay error can be measured between both adjacent and non-adjacent overlay marks (e.g., overlay error can be measured between overlay marks 800 and 802, 800 and 804, and 802 and 804). Such measurements can thereafter be utilized to correct overlay error between both adjacent and non-adjacent layers of a wafer.

Figure 9:
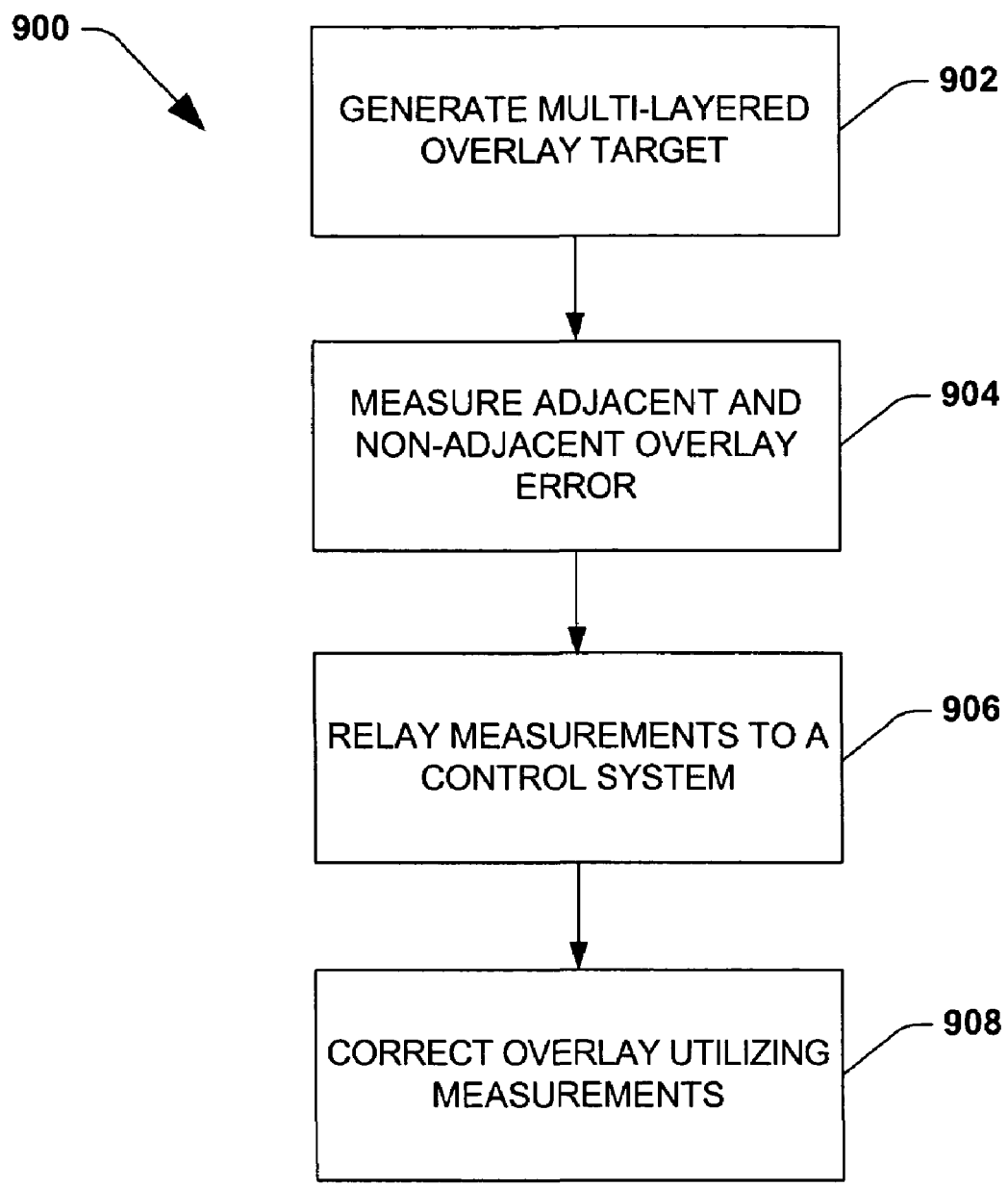
FIG. 9 is a representative flow diagram illustrating measuring and correcting overlay error between multiple layers of a wafer in accordance with an aspect of the present invention.

Turning now to FIG. 9, a methodology 900 for measuring and correcting overlay in more than two layers of an IC is illustrated. While, for purposes of simplicity of explanation, the methodology is shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

At 902, an overlay target representing multiple layers (e.g., more than two layers) of an IC is generated. For example, the overlay target can be a box-in-box structure, wherein boxes of substrate material decreasing in size are placed atop one another. More particularly, a larger box in the box-in-box structure will correspond to a lower layer on the wafer, and a smaller box will correspond to a higher layer on the wafer. Furthermore, other overlay target structures can be created in connection with the present invention. For instance, a frame-in-frame structure and a segmented-frame structure can be created to represent more than two layers of an IC.

At 904, overlay error between adjacent and non-adjacent layers is measured. For example, in an instance that an overlay target structure includes four layers, overlay error can be measured between adjacent layers (e.g., first and second, second and third, . . . ) as well as between a first and third layer, first and fourth layer, and second and fourth layer. The overlay error can be measured via optical microscopy, scanning electron microscopy, scatterometry, Fourier transform infrared scatterometry, and other suitable microscopic measuring and/or analysis techniques.

At 906, measurements relating to overlay between multiple layers are relayed to a control system via a cable, wireless network, etc. At 908 overlay error is corrected in to maintain design specifications and device tolerance of an IC based at least in part upon the measurements obtained at 904. For example, measurements relating to a first and second layer can be analyzed in a x-dimension and a y-dimension, followed by analysis of overlay regarding a first and third layer in both directions. Overlay between various other layers can also be analyzed, and the control system can correct overlay error between multiple layers accordingly (e.g., if overlay is more important in the x-dimension, more correction can be applied to such dimension).

Figure 10:
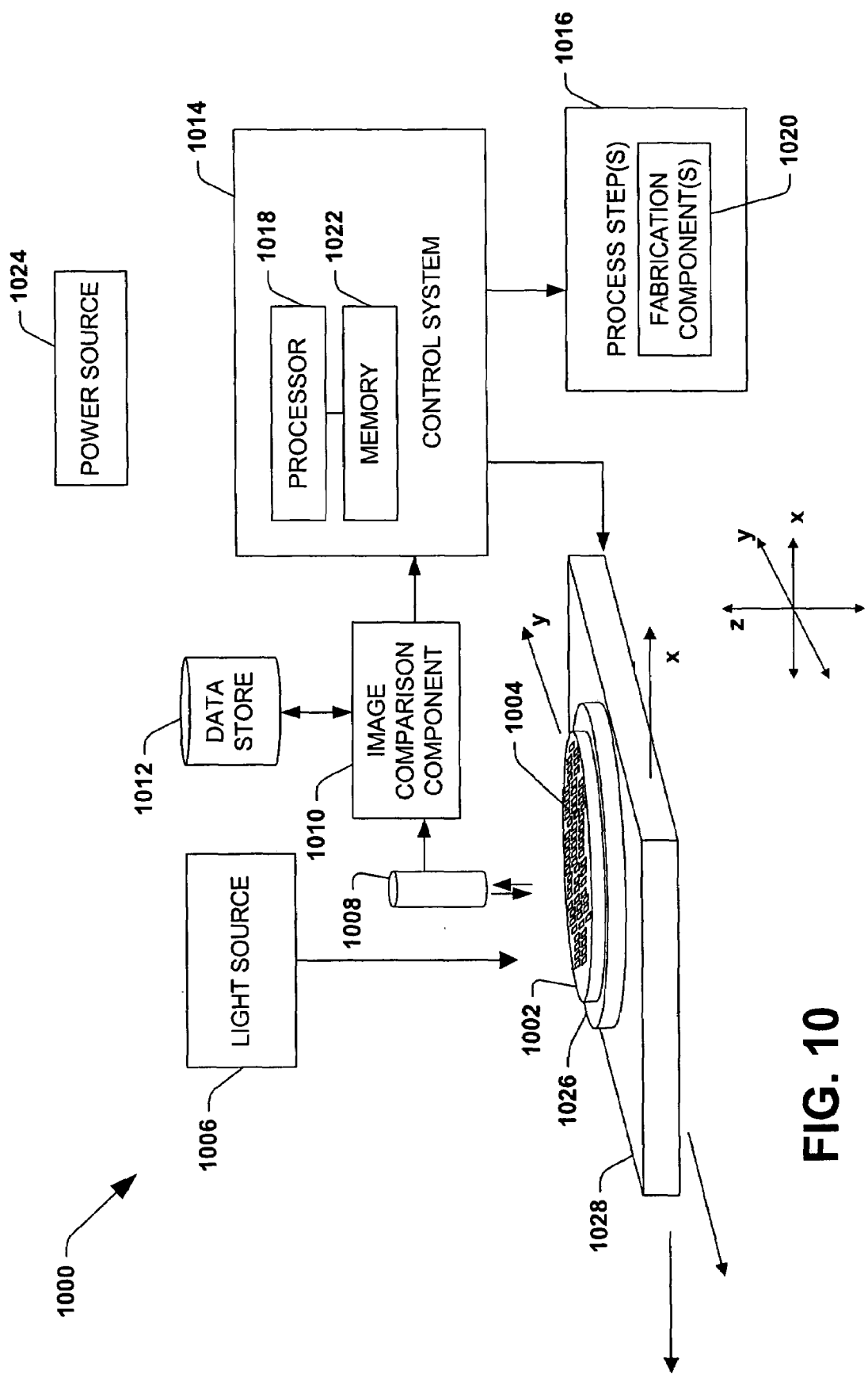
FIG. 10 is an exemplary system that measures and corrects overlay between multiple layers via optical microscopy techniques.

Now referring to FIG. 10, an exemplary system 1000 utilizing optical microscopy to measure and correct overlay error in multiple layers is illustrated. The system 1000 includes a wafer 1002 that comprises multiple dies 1004. The wafer 1002, and therefore the dies 1004, is made of more than two layers. One or more overlay targets (not shown) is located on the wafer, and a light source 1006 is utilized to illuminate at least a portion of the wafer 1002 that includes the overlay target(s). An optical microscope 1008 can thereafter obtain an image of such illuminated overlay target(s), and the image is relayed to an image comparison component 1010, which compares the image to images stored in a data store 1012. The comparison component 1010 can determine overlay error based at least in part upon results of comparison(s) between the captured image and one or more images from the data store 1012.

The analyzed overlay is thereafter relayed to a control system 1014 that effectuates controlling particular process step(s) 1016 to correct overlay error between multiple layers of the dies 1004. The control system 1014 includes a processor 1018 that is programmed to control and operate various fabrication component(s) 1020 within a wafer fabrication environment. A manner in which the processor 1018 can be programmed to carry out functions relating to the present invention will be readily apparent to those having ordinary skill in the art based on the description provided herein. A memory 1022 that is operatively coupled to the processor 1018 is also included in the control system 1014 and serves to store program code executed by the processor 1018 for carrying out operating functions of the fabrication component(s) 1020 as described herein. The memory 1022 includes, for example, read only memory (ROM) and random access memory (RAM). The RAM is the main memory into which the operating system and application programs are loaded. The memory 1022 also serves as a storage medium for temporarily storing measurements relating to overlay, as well as other data associated with measuring and correcting overlay between multiple layers. A power source 1024 provides operating power to the system 1000. Any suitable power source (e.g., battery, line power) may be employed to implement the present invention.

The wafer 1002 is held in a desirably position by a wafer holder 1026 on a wafer stage 1028 that is moveable in an x-direction and a y-direction. The wafer holder 1026 vacuum-absorbs the wafer 1002 and is provided for slight rotation relative to the stage 1028. The wafer holder 1026 and the stage 1028 are controlled by the control system 1014 to properly position the wafer 1002 relative to the optical microscope 1008. It is to be understood that the system 1000 can be a stand-alone metrology system, or alternatively can provide for in situ overlay measurement of multiple layers.

Figure 11:
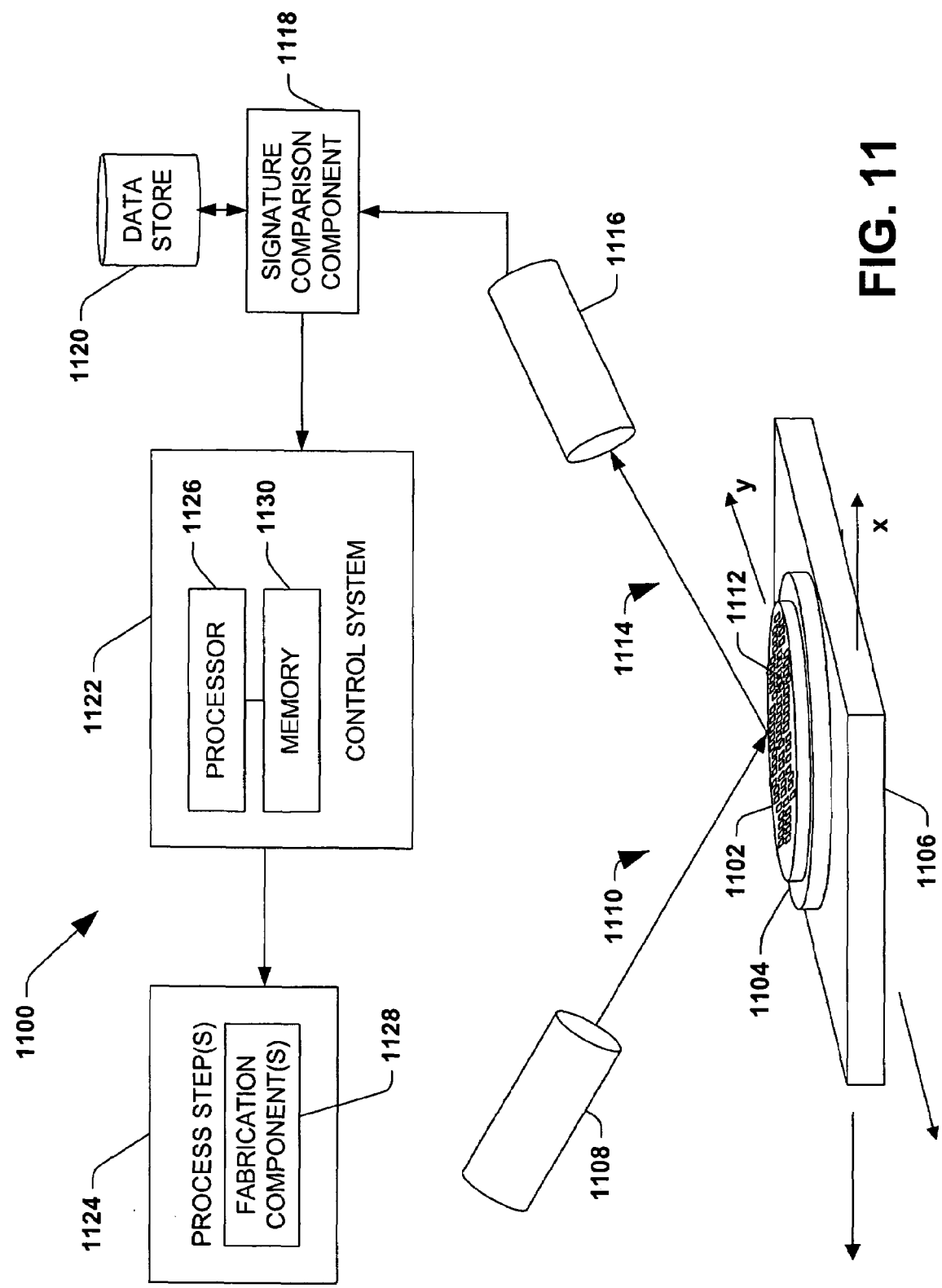
FIG. 11 is an exemplary system that measures and corrects overlay between multiple layers via scatterometry techniques.

FIG. 11 illustrates a system 1100 in accordance with another aspect of the present invention, wherein overlay between multiple layers can be measured and controlled via scatterometry techniques. A wafer 1102 is held in a desirable position by a wafer holder 1104 and a wafer stage 1106. A light source 1108 emits incident light 1110 at a particular overlay target (not shown) that has been created on the wafer 1102, wherein the overlay target represents multiple layers of one or more ICs 1112. The light reflected 1114 (or passed through) creates a particular signature, and a light receiver 1116 collects such signature.

The signature is thereafter received by a signature comparison component 1118, which compares this signature to known overlay signatures stored in a data store 1120. Such a comparison between the generated signature and a known signature provides an approximate, if not exact, measurement of actual overlay measurement between multiple layers. The analyzed overlay is thereafter relayed to a control system 1122 that effectuates controlling particular process step(s) 1124 to correct overlay error between multiple layers of the ICs 1112. The control system 1122 includes a processor 1126 which is programmed to control and operate various fabrication component(s) 1128 within a wafer fabrication environment. A memory 1130 that is operatively coupled to the processor 1126 is also included in the control system 1122 and serves to store program code executed by the processor 1126 for carrying out operating functions of the fabrication component(s) 1128. The control system 1122 can furthermore control the wafer holder 1104 and the wafer stage 1106 to properly align an overlay target (not shown) with the incident light 1110. Moreover, the system 1100 can be a stand-alone metrology system as well a system integrated with particular process step(s) to facilitate in situ measurement of overlay error between multiple layers.

Turning now to FIGS. 12–14, in accordance with one or more aspects of the present invention, a wafer 1202 (or one or more die located thereon) situated on a stage 1204 can be logically partitioned into grid blocks to facilitate measurement of overlay error as the wafer matriculates through a semiconductor fabrication process. This can facilitate selectively determining to what extent, if any, fabrication adjustments are necessary. Obtaining such information can also assist in determining problem areas associated with fabrication processes. FIG. 12 illustrates a perspective view of a stoppable stage 1204 supporting a wafer 1202. The wafer can be divided into a grid pattern as shown in FIG. 13. Each grid block (XY) of the grid pattern corresponds to a particular portion of the wafer 1202 (e.g., a die or portion of a die). The grid blocks are individually monitored for fabrication progress by measuring overlay error with optical microscopy, scatterometry, SEM, Fourier transform infrared scatterometry, or any other suitable metrology techniques.

This may also be applicable in order to assess wafer-to-wafer and lot-to-lot variations. For example, a portion P (not shown) of a first wafer (not shown) may be compared to the corresponding portion P (not shown) of a second wafer. Thus, deviations between wafers and lots can be determined in order to calculate adjustments to the fabrication components that are necessary to accommodate for the wafer-to-wafer and/or lot-to-lot variations.

In FIG. 13, one or more respective portions of a wafer 1202 ($X_1Y_1 \ldots X_{12}Y_{12}$) are monitored for overlay error utilizing optical microscopy, scatterometry, SEM, Fourier transform infrared scatterometry, or any other suitable metrology techniques. Exemplary measurements produced during fabrication produced during fabrication for each grid block are illustrated as respective plots. The plots can, for example, be composite valuations of signatures of overlay error. Alternatively, overlay error can be compare separately to respective tolerance limits.

As can be seen, the measurement at coordinate $X_7Y_6$ yields a plot that is substantially higher than measurement of other portions XY. This can be indicative of overlay, overlay error, and/or one or more critical dimensions outside of acceptable tolerances. As such, fabrication components and/or operating parameters associated therewith can be adjusted accordingly to mitigate repetition of this aberrational measurement. It is to be appreciated that the wafer 1202 and/or one or more die located thereon may be mapped into any suitable number and/or arrangement of grid blocks to effect desired monitoring and control.

FIG. 14 is a representative table of concurrently measured critical dimensions and overlay taken at various portions of the wafer 1202 mapped to respective grid blocks. The measurements in the table can, for example, be amalgams of respective critical dimension and overlay signatures. As can be seen, all the grid blocks, except grid block $X_7Y_6$, have measurement values corresponding to an acceptable value ($V_A$) (e.g., no overlay error is indicated and/or overlay measurements relating to multiple layers are within acceptable tolerances), while grid block $X_7Y_6$ has an undesired value ($V_U$) (e.g., overlay error between multiple layers is not within acceptable tolerances). Thus, it has been determined that an undesirable fabrication condition exists at the portion of the wafer 1202 mapped by grid block $X_7Y_6$. Accordingly, fabrication process components and parameters may be adjusted as described herein to adapt the fabrication process accordingly to mitigate the re-occurrence or exaggeration of this unacceptable condition.

Alternatively, a sufficient number of grid blocks may have desirable overlay measurements so that the single offensive grid block does not warrant scrapping the entire wafer. It is to be appreciated that fabrication process parameters may be adapted so as to maintain, increase, decrease and/or qualitatively change the fabrication of the respective portions of the wafer 1202 as desired. For example, when the fabrication process has reached a pre-determine threshold level (e.g., X % of grid blocks have acceptable overlay layer between multiple layers), a fabrication step can be terminated.

Figure 15:
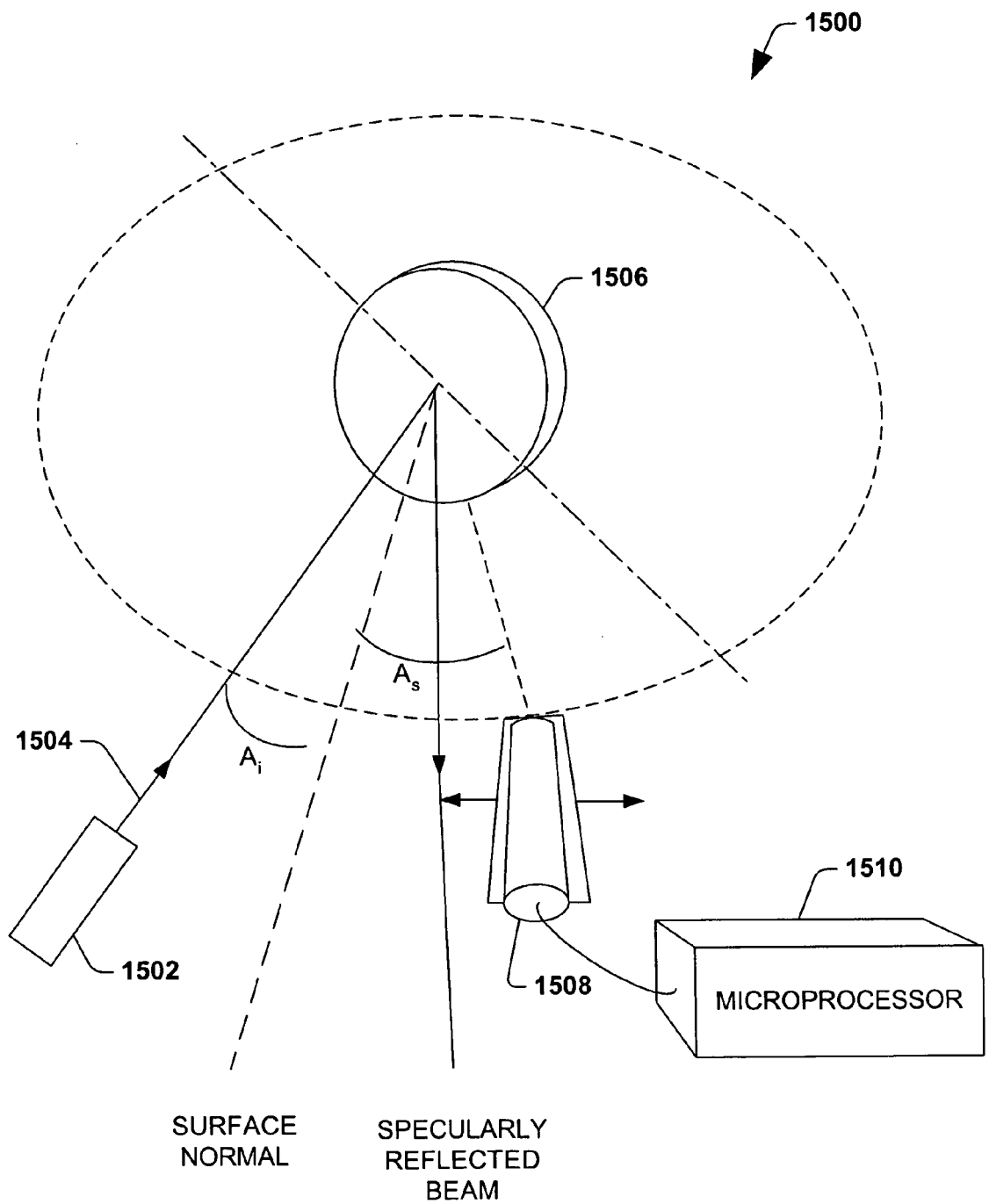
FIG. 15 illustrates a scatterometry system that can be utilized in connection with the present invention.

FIG. 15 illustrates an exemplary scatterometry system 1500 suitable for implementation with one or more aspects of the present invention. Light from a laser 1502 is brought to focus in any suitable manner to form a beam 1504. A sample, such as a wafer 1506, is placed in the path of the beam 1504 and a photo detector or photo multiplier 1508 of any suitable construction. Different detector methods and arrangements can be employed to determine the scattered and/or reflected power. A microprocessor 1510, or any suitable design, can be utilized to process detector readouts, including, but not limited to, intensity properties of the specularly reflected light, polarization properties of the specularly reflected light, and angular locations of different diffracted orders. Thus, light reflected from the sample 1506 can be accurately measured.

Figure 16:
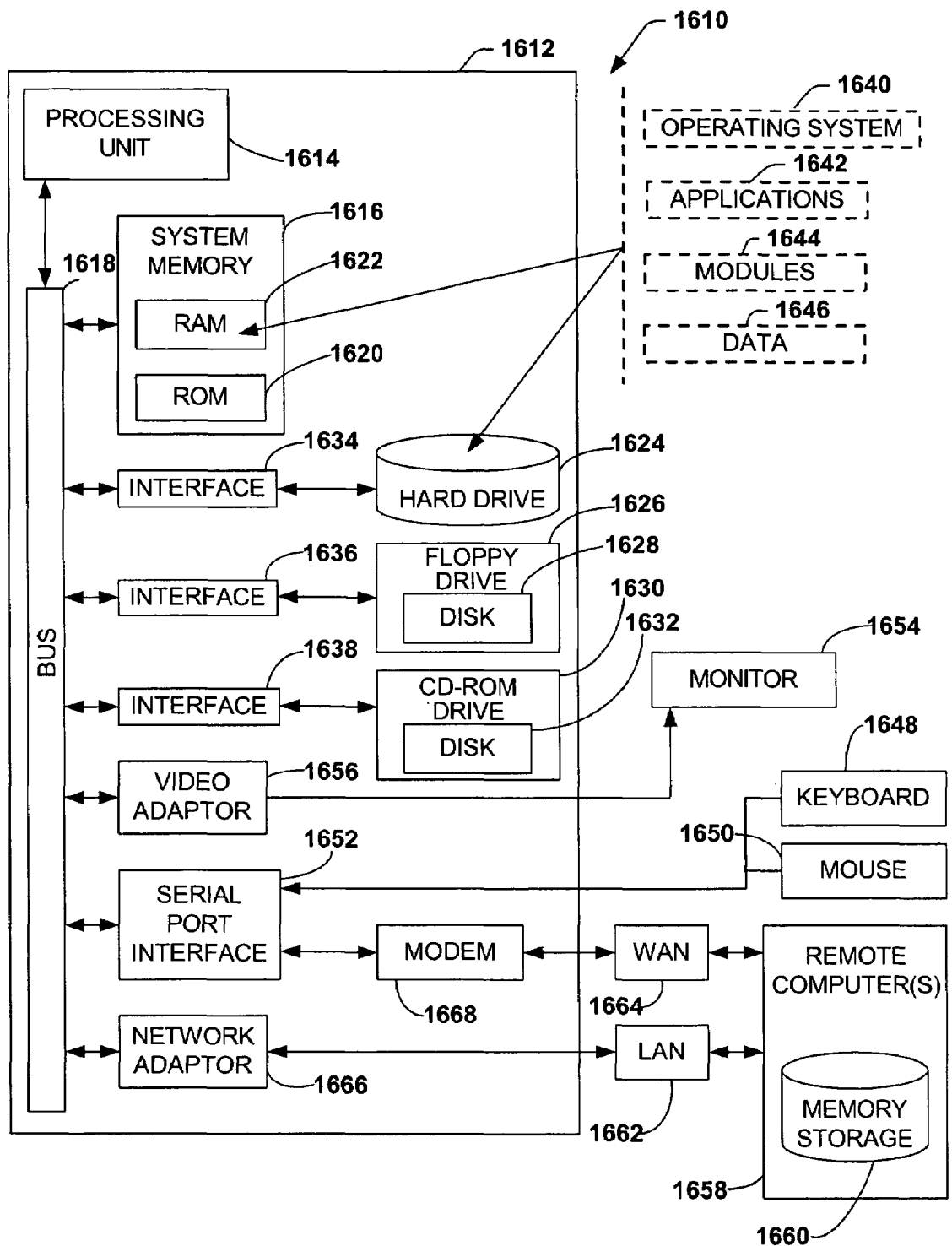
FIG. 16 is a schematic diagram of an exemplary computing environment for various aspects of the subject invention.

In order to provide additional context for various aspects of the present invention, FIG. 16 and the following discussion are intended to provide a brief, general description of a suitable computing environment 1610 in which the various aspects of the present invention can be implemented. While the invention has been described above in the general context of computer-executable instructions that may run on one or more computers, those skilled in the art will recognize that the invention also may be implemented in combination with other program modules and/or as a combination of hardware and software. Generally, program modules include routines, programs, components, data structures, etc. that perform particular tasks or implement particular abstract data types. Moreover, those skilled in the art will appreciate that the inventive methods may be practiced with other computer system configurations, including single-processor or multiprocessor computer systems, minicomputers, mainframe computers, as well as personal computers, hand-held computing devices, microprocessor-based or programmable consumer electronics, and the like, each of which may be operatively coupled to one or more associated devices. The illustrated aspects of the invention may also be practiced in distributed computing environments where certain tasks are performed by remote processing devices that are linked through a communications network. In a distributed computing environment, program modules may be located in both local and remote memory storage devices.

With reference to FIG. 16, an exemplary environment 1610 for implementing various aspects of the invention includes a computer 1612, including a processing unit 1614, a system memory 1616, and a system bus 1618 that couples various system components including the system memory to the processing unit 1614. The processing unit 1614 may be any of various commercially available processors. Dual microprocessors and other multi-processor architectures also can be used as the processing unit 1614.

The system bus 1618 can be any of several types of bus structure including a memory bus or memory controller, a peripheral bus, and a local bus using any of a variety of conventional bus architectures such as PCI, VESA, Microchannel, ISA, and EISA, to name a few. The system memory 1616 includes read only memory (ROM) 1620 and random access memory (RAM) 1622. A basic input/output system (BIOS), containing the basic routines that help to transfer information between elements within the computer 1612, such as during start-up, is stored in ROM 1620.

The computer 1612 further includes a hard disk drive 1624, a magnetic disk drive 1626 to read from or write to, for example, a removable disk 1628, and an optical disk drive 1630 for reading, for example, from a CD-ROM disk 1632 or to read from or write to other optical media. The hard disk drive 1624, magnetic disk drive 1626, and optical disk drive 1630 are connected to the system bus 1618 by a hard disk drive interface 1634, a magnetic disk drive interface 1636, and an optical drive interface 1638, respectively. The drives and their associated computer-readable media provide nonvolatile storage of data, data structures, computer-executable instructions, etc. for the computer 1612, including for the storage of broadcast programming in a suitable digital format. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment, and further that any such media may contain computer-executable instructions for performing the methods of the present invention.

A number of program modules may be stored in the drives and RAM 1622, including an operating system 1640, one or more application programs 1642, other program modules 1644, and program data 1646. The operating system 1640 in the illustrated computer is, for example, the "Microsoft® Windows® NT" operating system, although it is to be appreciated that the present invention may be implemented with other operating systems or combinations of operating systems, such as UNIX®, LINUX®, etc.

A user may enter commands and information into the computer 1612 through a keyboard 1648 and a pointing device, such as a mouse 1650. Other input devices (not shown) may include a microphone, an IR remote control, a joystick, a game pad, a satellite dish, a scanner, or the like. These and other input devices are often connected to the processing unit 1614 through a serial port interface 1652 that is coupled to the system bus 1618, but may be connected by other interfaces, such as a parallel port, a game port, a universal serial bus ("USB"), an IR interface, etc. A monitor 1654 or other type of display device is also connected to the system bus 1618 via an interface, such as a video adapter 1656. In addition to the monitor, a computer typically includes other peripheral output devices (not shown), such as speakers, printers etc.

The computer 1612 may operate in a networked environment using logical connections to one or more remote computers, such as a remote computer(s) 1658. The remote computer(s) 1658 may be a workstation, a server computer, a router, a personal computer, microprocessor based entertainment appliance (e.g., a WEBTV® client system), a peer device or other common network node, and typically includes many or all of the elements described relative to the computer 1612, although, for purposes of brevity, only a memory storage device 1660 is illustrated. The logical connections depicted include a local area network (LAN) 1662 and a wide area network (WAN) 1664. Such networking environments are commonplace in offices, enterprise-wide computer networks, intranets and the Internet.

When used in a LAN networking environment, the computer 1612 is connected to the local network 1662 through a network interface or adapter 1666. When used in a WAN networking environment, the computer 1612 typically includes a modem 1668, or is connected to a communications server on the LAN, or has other means for establishing communications over the WAN 1664, such as the Internet. The modem 1668, which may be internal or external, is connected to the system bus 1618 via the serial port interface 1652 to enable communications, for example, via POTS. The modem 1668 may also, in an alternative embodiment, be connected to the network adaptor 1666 to enable communications, for example, via DSL or cable. In a networked environment, program modules depicted relative to the computer 1612, or portions thereof, will be stored in the remote memory storage device 1660. It may be appreciated that the network connections shown are exemplary and other means of establishing a communications link between the computers may be used.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates measurement and correction of overlay between multiple layers of a wafer, comprising:
   an overlay target that represents overlay between three or more layers of a wafer;
   a measurement component that determines overlay error existent in the overlay target, and determines overlay error between the three or more layers of the wafer, where the measurement component comprises a comparison component that compares a captured signature with one or more stored signatures to facilitate determination of overlay error existent in the overlay target; and
   a control component that utilizes the overlay error determined by the measurement component to correct overlay error between the three or more layers of the wafer, the control component facilitating concurrent overlay correction of two or more wafers.

2. The system of claim 1, the control component provides more correction in a first dimension and less correction in a second dimension in an instance in which design rule requirements tolerate less overlay error in the first dimension when compared to the second dimension.

3. The system of claim 1, a substantial overlay correction between non-adjacent layers of the wafer in a first dimension correlates to a substantial overlay correction between adjacent layers of the wafer in a second dimension.

4. The system of claim 1, an insubstantial overlay correction between non-adjacent layers of the wafer in a first dimension correlates to an insubstantial overlay correction between adjacent layers of the wafer in a second dimension.

5. The system of claim 1, the control component manipulates at least one of temperature(s) associated with a process step, pressure(s) associated with a process step, concentration of gas(es) within a process step, concentration of chemical(s) within a process step, composition of gas(es) within a process step, composition of chemical(s) within a process step, flow rate of gas(es) within a process step, flow rate of chemical(s) within a process step, timing parameters associated with a process step, and excitation of voltages associated with a process step.

6. The system of claim 1, at least one of concentration, rate of flow, and degree of abrasiveness is controlled to correct overlay error.

7. The system of claim 1, the control component facilitates correction of rotational overlay error.

8. The system of claim 1, the measurement component and the control component are integrated with at least one process step to facilitate in situ correction of overlay error.

9. The system of claim 1, the overlay target has a structure of at least one of box-in-box, frame-in-frame, segmented frame, and periodic structure.

10. The system of claim 1, the overlay target comprises one or more gratings.

11. The system of claim 1, the measurement component comprising:
an optical microscope utilized to capture an image of the overlay target; and
a comparison component that compares the captured image with one or more stored images, wherein the comparison facilitates determination of overlay error existent in the overlay target.

12. The system of claim 1, the measurement component further comprising:
a light emitting component that delivers light incident to the overlay target; and
a light capturing component utilized to capture a signature that results from the incident light contacting the overlay target.

13. The system of claim 1, optical microscopy techniques are utilized to facilitate measurement of overlay error existent in the overlay target.

14. The system of claim 1, scatterometry techniques are utilized to facilitate measurement of overlay error existent in the overlay target.

15. The system of claim 1, scanning electron microscopy techniques are utilized to facilitate measurement of overlay error existent in the overlay target.

16. The system of claim 1, Fourier transform infrared scatterometry techniques are utilized to facilitate measurement of overlay error existent in the overlay target.

17. A stand-alone metrology unit comprising the system of claim 1.

18. The system of claim 1, the overlay target associated with a particular die on the wafer.

19. The system of claim 1, the wafer subdivided into a grid comprising a plurality of cells, wherein the grid facilitates measurement and recordation of overlay error at particular portions of the wafer.

20. The system of claim 19, the wafer discarded if a threshold percentage of cells exhibit a threshold level of overlay error.

21. A method for measuring and correcting overlay error in more than two layers of a wafer, the method comprising:
generating a multi-layered overlay target, wherein disparate layers of the overlay target represent disparate layers of the wafer;
delivering light incident to the overlay target;
capturing a signature that results from the incident light contacting the overlay target;
comparing the captured signature with one or more stored signatures to facilitate determination of overlay error existent in the overlay target;
approximating overlay error between layers on a wafer via measuring overlay error between representative layers of the overlay target;
correcting overlay error between layers of a wafer based at least in part on the measured overlay error existent in the representative layers of the overlay target; and
facilitating concurrent overlay correction of two or more wafers based at least in part upon the measured overlay error.

22. A stand-alone metrology unit utilizing the method of claim 21.

23. The method of claim 21, the layers of the wafer are non-adjacent layers.

24. The method of claim 21, the overlay error corrected via modifying one or more of temperature(s) associated with a process step, pressure(s) associated with a process step, concentration of gas(es) within a process step, concentration of chemical(s) within a process step, composition of gas(es) within a process step, composition of chemical(s) within a process step, flow rate of gas(es) within a process step, flow rate of chemical(s) within a process step, timing parameters associated with a process step, and excitation of voltages associated with a process step.

25. The method of claim 21, the layers of the wafer are adjacent layers.

26. The method of claim 21 further comprising:
substantially correcting overlay error between non-adjacent layers of the wafer in a first dimension; and
substantially correcting overlay error between adjacent layers of the wafer in a second dimension.

27. The method of claim 21, further comprising:
insubstantially correcting overlay error between non-adjacent layers of the wafer in a first dimension; and
insubstantially correcting overlay error between adjacent layers of the wafer in a second dimension.

28. The method of claim 21, further comprising providing a greater amount of overlay correction in one particular direction in comparison to a substantially perpendicular dimension.

29. A system that corrects overlay error between three or more layers of at least one wafer, comprising:
means for creating an overlay target, the overlay target representing three or more layers of a wafer;
means for delivering light incident to the overlay target;
means for capturing a signature that results from the light incident to the overlay target;

means for comparing the captured signature with one or more stored signatures to determine overlay error in the overlay target; and means for concurrently correcting overlay error between non-adjacent layers of the at least one wafer based at least in part on the measurements relating to the overlay target.

30. A system for correcting overlay error between three or more layers of at least one wafer, where the system comprises:

a measurement component that comprises:

a light emitting component that delivers light incident to the overlay target;

a light capturing component utilized to capture a signature that results from the incident light contacting the overlay target; and a comparison component that compares a captured signature with one or more stored signatures to determine overlay error associated with the overlay target; and a receiving component that receives measurements associated with overlay error between three or more layers of the wafer; and a control component that effectuates a concurrent overlay error correction in a first dimension between adjacent layers of the at least one wafer corresponding to a substantially similar overlay error correction in a second dimension between non-adjacent layers of the at least one wafer.

\* \* \* \* \*